United States Patent [19]

Silverman

[11] Patent Number: 4,882,537
[45] Date of Patent: Nov. 21, 1989

[54] METHOD AND APPARATUS FOR REDUCING INTERFERENCE IN AN ELECTRICAL RESISTANCE PROBE DURING ELECTROLYTIC PLATING

[75] Inventor: Herbert P. Silverman, Yellow Springs, Ohio

[73] Assignee: Rohrback Cosasco Systems, Inc., Santa Fe Springs, Calif.

[21] Appl. No.: 191,384

[22] Filed: May 9, 1988

[51] Int. Cl.⁴ .............................................. G01R 27/00
[52] U.S. Cl. ..................................... 324/65 R; 427/10
[58] Field of Search .............. 324/65 R, 65 P, 65 CR, 324/71.2; 427/8–10; 204/1 T, 404

[56] References Cited

U.S. PATENT DOCUMENTS

| | | | |
|---|---|---|---|
| 2,851,570 | 9/1958 | Schaschl | 201/63 |
| 2,864,925 | 12/1958 | Ellison | 201/63 |
| 2,978,364 | 4/1962 | Blaustein | 117/227 |
| 3,669,868 | 6/1972 | Lieber et al. | 204/228 |
| 4,331,699 | 5/1982 | Suzuki et al. | 427/8 |
| 4,331,702 | 5/1982 | Hieber et al. | 427/10 |
| 4,338,563 | 7/1982 | Rhoades et al. | 324/65 |
| 4,350,717 | 9/1982 | Araki et al. | 427/8 |
| 4,477,484 | 10/1984 | Paoletti et al. | 427/10 |
| 4,479,980 | 10/1984 | Acosta et al. | 427/10 |
| 4,514,681 | 4/1985 | Finley et al. | 324/65 |
| 4,592,921 | 6/1986 | Hieber et al. | 427/10 X |

Primary Examiner—Reinhard J. Eisenzopf
Assistant Examiner—Jack G. Harvey
Attorney, Agent, or Firm—Gausewitz, Carr & Rothenberg

[57] ABSTRACT

Measurements made with an electrical resistance sensor that is used for monitoring electrolytic plating are isolated from adverse effects of the strong plating currents flowing in the bath by momentarily disconnecting the resistive sensing element from the plating power source for a very short time interval during which resistance of the test element is measured.

15 Claims, 1 Drawing Sheet

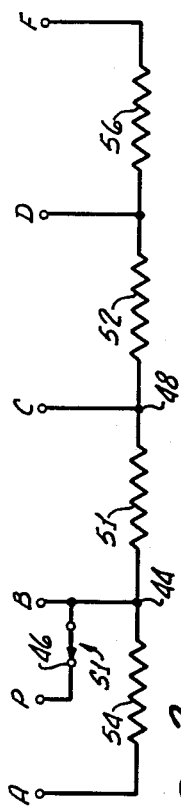
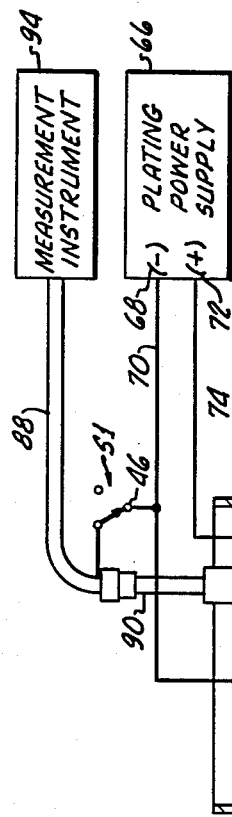
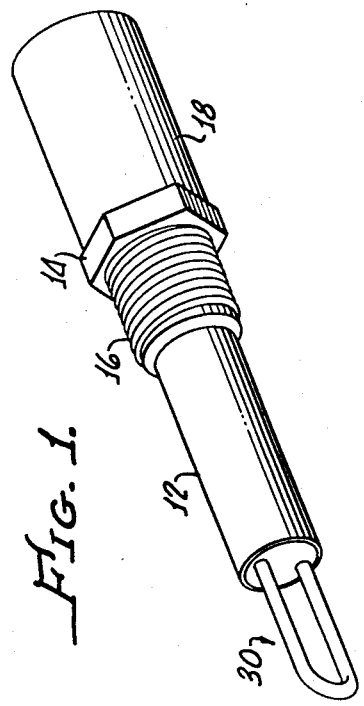
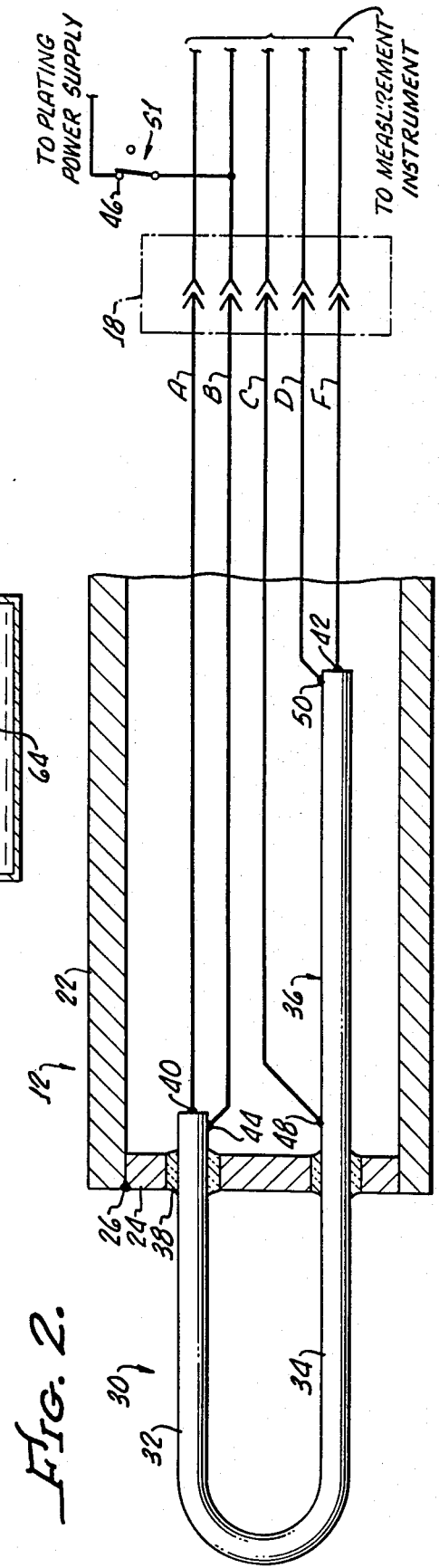

METHOD AND APPARATUS FOR REDUCING INTERFERENCE IN AN ELECTRICAL RESISTANCE PROBE DURING ELECTROLYTIC PLATING

BACKGROUND OF THE INVENTION

The present invention relates to electrical resistance sensors, and more particularly concerns sensors for monitoring plating processes. Monitoring of an electroplating process, as the process is carried out, is important to enable precise plating thicknesses and the high precision plating needed for many applications, such as use of precious metal platings. Precision measurement of plating thickness during electroplating has not been available.

Electrical resistance probes have been widely used for corrosion measurement, indicating by change of resistance the amount of metal that has been lost by corrosion or erosion over a period of time. A widely used sensor for this type of measurement is known under the trademark CORROSOMETER, manufactured by Rohrback Cosasco Systems, assignee of the present application. One such sensor employs a tubular metallic test element loop or wire, part of which operates as a reference element, made of the same material as the test element. The reference element is protected from the environment while the test element is exposed to the environment. A small alternating current is passed through the elements, and electrical resistance of each is measured while or after the sensor has been immersed in an environment in which a measurement is to be made. Because resistance varies with the amount of metal in the test element, measurement of test element resistance provides an indication of metal loss and therefore of corrosion.

Because resistance of the metal also changes with temperature, a reference element is provided, made of the same material as the test element and having the same temperature resistance characteristics. By this means changes in resistance of the test element that are due to long term relatively slow temperature variation may be eliminated by comparison of resistances of the test and reference elements. Other electrical resistance sensors may include a cylindrical metallic test element carrying an inner reference element made of the same material as the test element, with the interior of the test element filled with a thermally conductive electrically nonconductive compound, thereby providing physical support for the preferably very thin wall of the sensitive test element. It has been suggested to use such electrical resistance sensors to monitor plating operations. If used in a plating process, measurement of test element resistance would provide an indication of the plating thickness that has been accumulated on the test element. However, for measurement of thicknesses in an electroplating operation, such electrical resistance sensors must be connected to the high current plating power source, just as is the object to be plated. In such a situation, as the object is plated, the test element is plated, and its resistance decreases. Measurement of the decreasing resistance of the plated test element during progress of the electrolytic plating theoretically would provide a measurement of the plating thickness of the object. However, use of such electrical resistance measurement probes for an electrolytic plating bath has not been possible in the past. This is because the electrical current flowing in the electrolytic plating liquid is very large and causes so much interference with the measuring circuitry that measurement of resistance is not possible.

In a co-pending application, Ser. No. 821,013, filed Jan. 21, 1986, by Moore, Silverman and Bredow, and assigned to the assignee of the present application, there is described an electrical resistance sensor for monitoring electrolytic plating which avoids the problem of measurement interference caused by the high plating current. In the arrangement described in the co-pending application the test element is modified to provide a center tap which is connected to the plating power supply or a point of fixed potential. The central location of the tap causes plating currents flowing between the test element and the bath to flow in equal and oppositely directed components through the two halves of the test element on either side of the center tap, and thus the heavy interfering plating current effects are canceled from the resistance measurement.

SUMMARY OF THE INVENTION

In the present invention, adverse effects of the heavy currents in the plating bath are eliminated from the resistance measurement by a method and apparatus that avoids the need for any modification of the standard electrical resistance probe.

In carrying out principles of the present invention, in accordance with a preferred embodiment thereof, an electrical resistance sensor element is immersed in an electrolytic bath, together with an object to be electrolytically plated. A current path is provided between the plating power supply and the sensor element. When a measurement is made, the current path between the test element and the power supply is momentarily interrupted, and thus flow of adverse heavy bath current in the test element is also interrupted during the measurement time.

BRIEF DESCRIPTION OF THE DRAWINGS

FIG. 1 is a pictorial illustration of an electrical resistance sensor that may be employed in the practice of the present invention;

FIG. 2 is a section of a portion of the tip of the sensor of FIG. 1;

FIG. 3 is a simplified electrical schematic diagram of portions of the sensor resistive elements illustrating the switched connection of the test element; and FIG. 4 illustrates an electrolytic plating bath employing a sensor embodying the circuit of FIG. 3.

DETAIL DESCRIPTION OF THE INVENTION

As shown in FIG. 1, an exemplary tubular loop type corrosion sensor of a type known as a CORROSOMETER probe, manufactured by Rohrback Cosasco Systems is shown to include a tubular test element 30 mounted in a probe body 12 which is formed with a fitting 14 adapted to receive a suitable tool for rotating the probe body to cause a threaded neck 16 on the probe body to be turned into a threaded opening (not shown) of the wall of a tank or of a suitable fixture in the tank into which the sensor will extend to expose the tubular test element to the liquid of the electroplating bath within the tank. The body has a connector section 18 which includes one part of a detachable connector plug, having electrical terminals connected to various points on the test and reference elements, as will be described below.

FIG. 2 shows an enlarged fragmentary sectional view of the end of the tubular loop sensor of FIG. 1. Probe body 12 is shown as being formed of a tubular cylinder 22 having an end closed by a metallic header or disc 24, which is welded at its periphery 26 to the cylinder 22. A combined test and reference element includes a substantially U-shaped external portion having parallel legs 32,34, with leg 34 extending integrally through header 24 to form a reference element 36. Header disc 24 is formed with a pair of apertures for reception of the test element legs 32,34. The apertures are considerably larger than the diameter of the test element tubes, and the space between the walls of the header disc apertures and the tubes which extend there through is filled with a fused glass or other sealing material 38, which both electrically insulates the test and reference elements and hermetically seals the interior of cylinder 22.

In the illustrated embodiment the test and reference elements are formed from a single unitary length of thin wall electrically conductive hollow tubing. The tubing may be of a variety of materials and constructions. However, for increased sensitivity, the tubing forming the test and reference elements is preferably formed, as described in detail in the above-mentioned co-pending application, of a high resistivity electrically conductive substrate (composed substantially entirely of a stainless steel, for example), with the reference element having a reference coating electroplated directly thereon. The conductive substrate of the test element has a high electrical resistivity, much higher than resistivity of the material (which may be copper, gold or silver, for example) being plated upon the object, and thus sensitivity of the measurement of the material coated upon the substrate during the plating operation is greatly enhanced. For use as a plating monitor, the material to be plated on the object will also be plated directly upon the electrically conductive substrate of the test element, thereby increasing the thickness of the test element and decreasing its resistance. Measurement of this decrease in resistance will then provide a measurement of the thickness of the coating that has been electrolytically plated upon the substrate.

For use in measurement of resistance of the test element, terminals A and F, which are mounted within the connector portion 18, are connected by insulated electrical leads to points 40 and 42 (FIG. 2) respectively on the respective ends of the integral tubular element. Terminal B is also connected to one end of the tubular test element at a point 44 adjacent point 40. Terminal C is connected at point 48 adjacent the header disc to an end of the reference element and to one end of the test element. Terminal D is connected to the end of the reference element at point 50 adjacent point 42. Terminals A and F are connected to a source of alternating current (not shown in FIG. 2), providing a relatively small energizing current flowing through both test and reference elements. Measurement of resistance of the test element 32 is made between points 44 and 48, terminals B and C, and measurement of the resistance of the reference element 36 is made between points 48 and 50, between terminals C and D. Measurement of test element resistance involves calculation of the ratio of measured resistance of the test element to measured resistance of the reference element. The latter is protected from the electrolytic bath and therefore is not plated by the bath, whereas the test element is exposed to the bath and is plated. As the test element is plated, its thickness increases and its resistance decreases, whereas the protective reference element maintains a fixed resistance except for temperature fluctuations. As well known, both resistance measurements are subject to fluctuation with varying temperature. Preferably the reference and test elements have the same temperature coefficient of resistance (as by making the two elements integral or of the same material) and experience the same variation in resistance with temperature changes. Therefore, that portion of the measured variation in resistance of the test element which is due to variation in temperature is eliminated from the measurement by use of the ratio of measured test element resistance to measured reference element resistance.

Electrical resistance probes presently in use, having configurations exemplified by the illustrations of FIGS. 1 and 2, have employed various types of sensing elements. For example, the elements of sensor 30 of FIGS. 1 and 2 may take the form of the illustrated loop of thin wall tubing formed of an electrically conductive metal. Alternate configurations of such sensors include loops of solid wire, loops of flat metal strip, or straight wall, hollow cylinder having a relatively thick sensitive metal disc closing the end of the cylinder. These are configurations well known in the electrical resistance sensor art, and are shown, for example, in U.S. Pat. Nos. 4,338,563 and 4,514,681. The loops or cylinder are exposed to the environment in which a measurement is to be made, and may include an integral reference element, such as reference element 36 of FIG. 2 mounted within the probe body and protected from the environment as previously described.

Electrical resistance measuring methods that have been previously known are not capable of use for monitoring of electroplating, except for the arrangements shown in the above-identified prior co-pending application. It has been found that currents existing in the electrolytic bath, e.g., the plating current, flow through the sensing element of prior devices and produce noise (to the resistance measurement circuit) of such magnitude as to substantially mask the desired resistance measuring signal. The resistance measuring signals are relatively small compared to the plating currents, and thus any measurement signals are overwhelmed by the heavy currents in the bath. Presently employed methods for monitoring of electrolytic plating include empirical measurement. Other arrangements for measuring electrolytic plating also fail to provide a real time or ongoing plating measurement that indicates the thickness of plating as it occurs.

The arrangement of the above-identified prior co-pending application solves these problems with a probe that is slightly modified to include special leads connected to the test element for eliminating or balancing out the stray noise currents induced in the test element by the electrolytic bath.

According to the present invention, stray noise currents induced in the electrical resistance test element by the liquid environment in which it is immersed are allowed to flow in the test element during most of the period during which the test element is being plated together with the object that is immersed in the bath with the test element. However, no measurement of resistance of the test element is made while such stray noise currents are flowing in the test element. When a measurement is to be made, the test element is disconnected from the circuit of the plating power supply for a very short interval of time, thereby interrupting flow of stray noise current in the test element for a short time and enabling the measurement of test element resistance to be made without being in any way affected by the heavy plating currents flowing in the bath.

Illustrated in FIG. 3 is a simplified schematic diagram of an electrical resistance sensor of the type described in connection with FIGS. 1 and 2. This sensor is the same as the sensor described above, except for the addition of a switch S1 connected to the point 44 to which the measurement terminal B is connected. Switch S1 is operable to selectively connect test element connecting point 44 to a terminal 46 of switch S1 or to open the switch. Terminal 46 is connected to the electrolytic plating power supply, indicated at P in FIG. 3.

In FIG. 3 resistor 51 indicates the test resistance, resistor 52 the reference resistance, and portions of the sensor element between the AC excitation terminals A and F and the measurement terminals B and D respectively are indicated by resistors 54,56. In effect the circuit is a simple series circuit of the four resistors all connected in end-to-end relation to one another and to the AC excitation terminals A and F.

During normal plating operation, the switch S1 is in the position illustrated, connecting test element 44 to terminal P, which in turn is connected to the plating power supply, as will be described below. Thus the connecting point 44 is also connected, in parallel, to the plating power supply during the normal plating operation. A timing program is employed to cyclically repeat periods of switch operation. In a major part of the switch cycle, no measurement is made, and switch S1 is in the illustrated position, connecting the test element to the plating power supply. In a second part of the switch cycle, a short measurement is made, during which the switch is in open position to disconnect the test element from the power supply. The period of measurement, that is the period in which the switch S1 has its arm disconnected from switch terminal 46, is very small compared to the time during which the switch is in the illustrated position connected to the plating power supply. Thus loss of plating of test element that occurs during the very brief measurement period will introduce only a very small or negligible error.

An electrolytic plating operation employing the monitoring system described in connection with FIG. 3 is illustrated schematically in FIG. 4. As shown in FIG. 4, an object 58 that is to be plated is immersed in an electrolytic bath 60, confined in a tank 62, in which is also immersed an anode 64. A DC source of plating voltage 66, the plating power supply, has one terminal, such as its negative terminal 68, connected via a lead 70 to the object 58 that is to be plated. The other terminal, the positive terminal 72 of power supply 66, is connected via a lead 74 to the anode 64. A sensor, generally indicated at 82, constructed substantially as described in connection with FIGS. 1, 2 and 3, is mounted so as to have its loop test element 86 immersed within the bath, preferably at a position close to the object 58. Test element 86, as previously described, may include a loop of thin wall tubing, a loop of solid wire, or a strip loop or a cylindrical test element. Test element 86 may be the previously described conductive, high resistivity substrate (such as a 316 stainless steel, or similar metal, for example) that may or may not initially have an electroplated coating. The various leads connected with terminals A, B, C, D and F of FIG. 3 are carried in a cable 88, which connects the probe to a measuring instrument 94. The lead connected to terminal B and to point 44 on the test element is also connected via terminal 46 of switch S1 (when the switch is closed) to the lead 70 from the plating power supply. During plating operation, the switch is in the closed position illustrated, and current will flow from the plating power supply through lead 70 to the object 58 and also in parallel with the object to the test element 86, via the switch S1. For the short measurement interval, the switch is moved to its open position, thereby disconnecting the probe from the bath and its currents.

During a normal plating operation current flows from the plating power supply through the object 58 and test element 86 in parallel, thence through the electrolytic bath to the anode and back to the power supply. During this time the very large current flowing through the test element due to the plating power supply will mask the much smaller AC excitation signal and any resistance measurement based thereon. However, at this time no attempt is made to measure resistance of the test element. For a measurement of resistance of the test element to be made, the switch S1 is thrown to its open position, interrupting flow of current from the plating power supply through the test element for a very short interval of time. Now, as no plating current is flowing through the test element 86, a measurement of resistance of the test element may be readily made without being substantially affected by the unwanted current or noise caused by currents flowing in the electrolytic bath. In the absence of any such noise current flowing in the test element, the resistance of the latter may be readily measured on the basis of the relatively small voltage produced by the exciting source connected to terminals A and F of the sensor.

The above described plating monitor sensor, operated as described, may employ many other physical configurations in addition to those described in connection with the description of the corrosion probe.

In the practice of the described embodiments of the invention, it is preferred that the switch S1 be closed (so that the test element is subjected to plating) a minimum of between 90 to 95 percent or more of the time of the entire plating operation. The time of a plating operation may vary considerably from perhaps ten minutes to several hours, or a day or more. Thus the time of switch opening for making a measurement free of noise due to plating currents is chosen to be 90 to 95 percent or more of the total plating time. Measurements may be made periodically during the plating operation on a regular basis, or on a variable reading cycle. For example, for a short ten minute total plating time, a measurement might be made approximately every two minutes, with each measurement requiring approximately three to ten seconds. In other words, for a total plating operation which is expected to require about ten minutes, after each two minute interval, switch S1 would be opened to eliminate the plating current noise in the measurement, and a measurement would be made. With some instruments a measurement may be made in as little as three seconds. With such a regular measurement interval for a ten minute plating operation, information concerning plating thickness would be available at a number of times during the plating operation. For such an arrangement, a total reading time or open switch time of twenty-five to fifty seconds would occur (for a reading time of five to ten seconds for each open switch reading), and such a total open switch time would be well within the 90 percent desirable minimum switch closed time. For longer plating times and less frequent measurements, the percentage of time that switch S1 is open decreases, and, therefore, measurement precision increases.

A variable reading cycle is available to provide the plating operator with more information toward the end of the plating cycle than earlier. This is accomplished by allowing the operation (the above-mentioned exemplary ten minute plating cycle) to proceed for the first five minutes without any monitoring and without opening the switch, and then, after lapse of the first five minutes, the switch is opened at one minute intervals for a period of five to ten seconds each until the plating thickness desired is reached. Again the total switch open time is within 90 percent of the total plating time, and thus errors in the reading are kept to an acceptable minimum value. It will be understood, of course, that all of the times and periods described above are stated solely for purposes of exposition, and that these may be varied according to degrees of precision and other factors that relate to a desired plating operation.

The sensor employed in plating monitoring may be readily reused by stripping the plating material from the substrate after use of the monitor. This is more readily accomplished where the substrate is a stainless steel, which is insensitive to cleaning agents that may be employed. Such probe test element refurbishing is more particularly described in the aboveidentified co-pending patent application.

The foregoing detailed description is to be clearly understood as given by way of illustration and example only, the spirit and scope of this invention being limited solely by the appended claims.

What is claimed is:

1. A method of monitoring a process for plating a selected material upon an object immersed in an electrolytic bath comprising the steps of:
    forming a monitoring sensor with an electrically conductive test element,
    immersing the monitoring sensor in said electrolytic bath with the test element in contact with the bath,
    starting the plating process to cause plating current to flow in current paths between a power supply and the monitoring sensor and between the power supply and the object to be plated, thereby to cause both the object and test element to be plated with said material,
    momentarily interrupting flow of current between the power supply and the monitoring sensor, and
    while said current is interrupted measuring the electrical resistance of said test element.

2. The method of claim 1 wherein said plating operation is carried out for a first time, and wherein said momentary interruption of current lasts for a time not greater than about ten percent of said first time.

3. The method of claim 1 wherein said step of momentarily interrupting is carried out a number of times during said first time, and wherein said momentary interruptions last for a total time not greater than about ten percent of said first time.

4. The method of claim 1 wherein said step of forming a monitoring sensor comprises forming a substrate composed substantially of material having a high resistivity, and wherein said selected material has a low resistivity.

5. The method of claim 1 wherein said step of momentarily interrupting flow of current between the power supply and the monitoring sensor is performed while current flows in the current path between the power supply and the object to be plated.

6. In combination with a vessel that confines a fluid in which electrical currents flow, an electrical resistance sensor comprising:
    a test element immersed in said fluid, said test element being subject to noise currents induced therein by said electrical currents,
    means for providing an electrical current path between said test element and a point of fixed potential,
    means for momentarily interrupting said current path, and
    means for measuring electrical resistance of said test element while said current path is interrupted.

7. The invention of claim 6 wherein said test element comprises a substrate composed substantially entirely of a stainless steel.

8. A resistance probe for use in monitoring electrolytic plating of an object immersed in an electrolytic bath and connected to a plating power source, said probe comprising:
    an electrically conductive test element constructed and arranged to be immersed in the electrolytic bath with the object to be plated,
    means for electrically connecting the plating power source to said test element to provide a current path between the power source and the test element for a predetermined plating period,
    means for momentarily interrupting said current path for a time that is not more than about ten percent of said period, and
    means for measuring resistance of said test element while said current path is interrupted.

9. The probe of claim 8 wherein said test element comprises a stainless steel substrate.

10. A method of monitoring electroplating of an object immersed in an electrolytic bath and connected to an electrolytic current power supply, said method comprising the steps of:
    immersing an electrically conductive test element in the bath,
    providing a current path between the test element and the power supply,
    momentarily interrupting the current path, and
    measuring electrical resistance of the test element while the current path is interrupted.

11. The method of claim 10 wherein said current path is interrupted for a time not more than about ten percent of the total time that the object is immersed in the bath and connected to the power supply.

12. A system for electroplating an object and monitoring the electroplating as it occurs, said system comprising:
    a tank,
    an electrolytic liquid in the tank,
    a plating power supply,
    means for providing a first current path between the power supply and an object immersed in the electrolytic liquid, and providing a second current path between the power supply and an electrode immersed in the electrolytic liquid,
    an electrical resistance measuring element immersed in the electrolytic liquid,
    a resistance measuring instrument connected to the measuring element,
    means for providing a third current path between said plating power supply and said electrical resistance measuring element, and means for momentarily interrupting said third current path, whereby measurement of electrical resistance of said resistance element can be made while current flow between the electrolytic bath and the measuring element is interrupted.

13. The system of claim 12 wherein said means for interrupting the third current path comprises means for disconnecting the measuring element from the power supply for a total time not greater than about ten percent of a total plating time of said object.

14. The system of claim 12 wherein said measuring element comprises a substrate of stainless steel.

15. The system of claim 12 including means for maintaining flow of current in said first and second current paths while said third current path is momentarily interrupted.

* * * * *